(12) United States Patent
Arányi et al.

(10) Patent No.: US 6,969,723 B2
(45) Date of Patent: Nov. 29, 2005

(54) AMINOQUINOLINE AND AMINOPYRIDINE DERIVATIVES AND THEIR USE AS ADENOSINE A3 LIGANDS

(75) Inventors: Peter Arányi, Budapest (HU); László Balázs, Dunakeszi (HU); Mária Balogh, Dunakeszi (HU); Imre Bata, Budapest (HU); Sándor Bátori, Budapest (HU); Lajos T. Nagy, Budapest (HU); Geza Tímári, Vecsés (HU); Kinga Boér, Budapest (HU); Olivier Finance, Montpellier (FR); Zoltán Kapui, Budapest (HU); Endre Mikus, Budapest (HU); Zsuzsanna Szamosvölgyi, Budapest (HU); Gábor Szeleczky, Budapest (HU); Katalin Urbán-Szabó, Budapest (HU)

(73) Assignee: Sanofi - Aventis, Paris (FR)

( * ) Notice: Subject to any disclaimer, the term of this patent is extended or adjusted under 35 U.S.C. 154(b) by 0 days.

(21) Appl. No.: 10/478,721

(22) PCT Filed: May 29, 2002

(86) PCT No.: PCT/HU02/00048

§ 371 (c)(1),
(2), (4) Date: May 13, 2004

(87) PCT Pub. No.: WO02/096879

PCT Pub. Date: Dec. 5, 2002

(65) Prior Publication Data

US 2004/0186133 A1 Sep. 23, 2004

(30) Foreign Application Priority Data

May 31, 2001 (HU) .............................. 0102279
Mar. 1, 2002 (HU) .............................. 0200774

(51) Int. Cl.[7] ............... C07D 215/38; C07D 211/72; A61K 31/47
(52) U.S. Cl. ............ 514/313; 514/352; 514/353; 546/159; 546/160; 546/161; 546/279.7; 546/308
(58) Field of Search ................ 514/313, 352, 514/353; 546/159, 160, 161, 279.7, 308

(56) References Cited

FOREIGN PATENT DOCUMENTS

| DE | 265143 A1 | 2/1989 |
|---|---|---|
| EP | 1180518 | 2/2002 |
| WO | WO 95/11244 | 4/1995 |

OTHER PUBLICATIONS

Graf, Chem. Berichte, 64, 1931, pp. 21–26.
Gewald et al., J. Pract. Chem./Chem.–Ztg. 334(1), 1992, pp. 89–91.
Gewald K. et al., Chemical Abstracts, abstract No. 255453f, vol. 116, No. 25, Jun. 22, 1992.
Gewald K. et al., Chemical Abstract Plus, abstract No. 116:255453 (1992).
Sarhan, Abd El–Wareth A.O. et al., Chemical Abstracts, abstract No. 69693x. vol. 136 (2001).
Sarhan, Abd El–Wareth A.O. et al., Chemical Abstracts Plus, abstract No. 136:69693 (2001).

*Primary Examiner*—D. Margaret Seaman
(74) *Attorney, Agent, or Firm*—Jiang Lin

(57) ABSTRACT

Compounds of general formula (I), wherein $R^4$ and $R^5$ stand for hydrogen atom or form together an 1,3-butadienyl group, optionally substituted by a methylenedioxy group or one or more straight or branched $C_{1-4}$ alkyl group, straight or branched $C_{1-4}$ alkoxy group, hydroxy group or halogen atom; are strong adenosine $A_3$ receptor ligands preferably antagonists.

(I)

Figure 1:
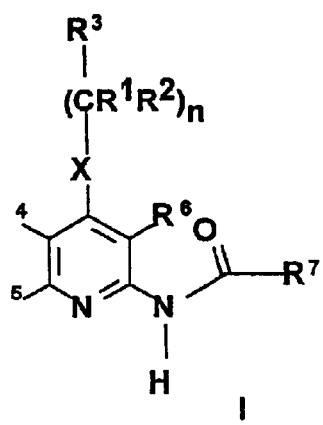

$$\begin{array}{c} R^3 \\ | \\ (CR^1R^2)_n \\ | \\ X \end{array}$$

with pyridine ring bearing $R^4$, $R^5$, $R^6$ and N–H–C(=O)–$R^7$ substituent.

18 Claims, 2 Drawing Sheets

Reaction scheme 1.

AMINOQUINOLINE AND AMINOPYRIDINE DERIVATIVES AND THEIR USE AS ADENOSINE A3 LIGANDS

The present invention relates to adenosine $A_3$ receptor ligands of the general formula (I), within those preferably antagonists, as well as their salts, solvates and isomers, and the pharmaceutical compositions containing them, to the use of the compounds of the general formula (I), as well as their salts, solvates and isomers, to the preparation of the compounds of the general formula (I) and their salts, solvates and isomers, furthermore to the new intermediates of the general formulae (II) (III) and (IV) and to the preparation thereof.

Adenosine is a well-known component of several endogenous molecules (ATP, $NAD^+$, nucleic acids). Besides, it plays an important regulatory role in many physiological processes. The effect of adenosine on heart function was discovered already in 1929. (Drury and Szentgyörgyi, J Physiol 68:213, 1929). The identification of an increasing number of physiological functions mediated by adenosine and the discovery of new adenosine receptor subtypes give possibilities for therapeutic application of specific ligands (Poulse, S. A. and Quinn, R. J. Bioorganic and Medicinal Chemistry 6:619, 1998).

To date, the receptors for adenosine have been classified into three main classes: $A_1$, $A_2$ and $A_3$. The $A_1$ subtype is partly responsible for inhibiting the adenylate cyclase by coupling to $G_i$ membrane protein, partly influences other second messenger systems. The $A_2$ receptor subtype can be subdivided into two further subtypes—$A_{2a}$ and $A_{2b}$—, which receptors stimulate the adenylate cyclase activity. The sequence of adenosine $A_3$ receptors have been recently identified from rat testis cDNA library. Later it was proved that it corresponds to a novel, functional adenosine receptor. The activation of the $A_3$ receptors is connected also with several second-messenger systems: inhibiting of adenylate cyclase, stimulating of phospholipase C and D.

The adenosine receptors are found in several organs and regulate their functions. Both $A_1$ and $A_{2a}$ receptors play important roles in the central nervous system and cardiovascular system. In the CNS, the adenosine inhibits the release of synaptic transmitters which effect is mediated by $A_1$ receptors. In the heart, also the $A_1$ receptors mediate the negative inotropic, chronotropic and dromotropic effects of adenosine. The adenosine $A_{2a}$ receptors located relatively in a higher amount in the striatum, display a functional interaction with dopamine receptors in regulating the synaptic transmission. The $A_{2a}$ adenosine receptors on endothelial and smooth muscle cells are responsible for adenosine-induced vasodilation.

On the basis of mRNA identification, the $A_{2b}$ adenosine receptors are widely distributed in different tissues. They have been identified almost in every cell type, but its expression is the highest in the intestine and the bladder. This subtype probably also has important regulatory function in the regulation of the vascular tone and plays a role in the function of mast cells.

Contrary to $A_1$ and $A_{2a}$ receptors, where the tissue distribution was detected on the protein level, the presence of $A_{2b}$ and $A_3$ receptors was detected on the basis of their mRNA level. Expression levels for $A_3$ adenosine receptors are rather low comparing to other subtypes and highly species dependent. $A_3$ adenosine receptors are expressed primarily in the central nervous system, testis, immune system and appear to be involved in the modulation of mediator release from mast cells in immediate hypersensitivity reaction.

The $A_3$ antagonists published so far in the literature belong to the groups of flavonoides, 1,4-dihydropyridine derivatives, triazoloquinazolines, thiazolonaphthyridines and thiazolopyrimidines. The present invention relates to a novel type of effective $A_3$ antagonists, which have the aminoquinoline structure.

For therapeutic use it is essential to ensure that the molecule does not bind, or bind only in the case of very high concentration to the $A_1$, $A_{2a}$ and $A_{2b}$ sub-types of the adenosine receptor. Our present invention relates to the compounds of the general formula (I) as well as their salts, solvates and isomers which have great selectivity for the $A_3$ subtype of the adenosine receptor.

Our aim was to prepare $A_3$ ligands first of all with quinoline structure, and within those preferably antagonists, which have strong antagonistic effect and show high selectivity for the $A_3$ receptor, ie. they inhibit the $A_3$ receptor in much lower concentration than they inhibit the $A_1$, $A_{2a}$ and $A_{2b}$ receptors. Further aims were to have stability, bioavailability, therapeutic index and toxicity data which make possible to develope the new compounds into drug substances and that due to their favourable enteral absorbtion the compounds can be applied orally.

We have found that the compounds of the general formula (I)—wherein $R^1$ stands for hydrogen atom or a straight or branched $C_{1-4}$ alkyl group;

$R^2$ stands for hydrogen atom or a straight or branched $C_{1-4}$ alkyl group;

$R^3$ stands for hydrogen atom or a straight or branched $C_{1-4}$ alkyl group, or a phenyl group, thienyl group, or furyl group, optionally substituted by one or more straight or branched $C_{1-4}$ alkyl group, straight or branched $C_{1-4}$ alkoxy group, or halogen atom, or for a 5- or 6 membered heteroaromatic ring—containing one, two or three nitrogen atoms or one nitrogen atom and one oxygen atom or one nitrogen atom and one sulphur atom— optionally substituted by one or more straight or branched $C_{1-4}$ alkyl group, straight or branched $C_{1-4}$ alkoxy group, or halogen atom;

$R^4$ and $R^5$ stand for hydrogen atom or form together an 1,3-butadienyl group, optionally substituted by a methylenedioxy group or one or more straight or branched $C_{1-4}$ alkyl group, straight or branched $C_{1-4}$ alkoxy group, hydroxy group or halogen atom;

$R^6$ stands for hydrogen atom or a cyano group, aminocarbonyl group, $C_{1-4}$ alkoxycarbonyl group, or carboxy group;

$R^7$ stands for hydrogen atom or a straight or branched $C_{1-4}$ alkyl group, or a phenyl group, benzyl group, thienyl group or furyl group, optionally substituted by a methylenedioxy group, or one or more straight or branched $C_{1-4}$ alkyl group, straight or branched $C_{1-4}$ alkoxy group, hydroxy group, trifluoromethyl group, cyano group or halogen atom, or for a 5 or 6 membered heteroaromatic ring—containing one, two or three nitrogen atoms or one nitrogen atom and one oxygen atom or one nitrogen atom and one sulphur atom— optionally substituted by one or more straight or branched $C_{1-4}$ alkyl group, straight or branched $C_{1-4}$ alkoxy group, or halogen atom, X stands for a —$CH_2$— group, —NH— group, —$NR^8$— group, or a sulphur atom or an oxygen atom or a sulpho group or a sulphoxy group—wherein $R^8$ stands for a straight or branched $C_{1-4}$ alkyl group or $C_{3-6}$ cycloalkyl group—;

n stands for zero, 1 or 2—and their salts, solvates, and isomers and the salts, solvates of the latter, fulfill the above criteria.

Detailed meanings of the above listed substituents are as follows:

By a straight or branched $C_{1-4}$ alkyl group we mean methyl-, ethyl-, propyl-, isopropyl-, butyl-, isobutyl-, secondary-butyl-, tertiary-butoxy-, preferably ethyl- or methyl group.

By a straight or branched $C_{1-4}$ alkoxy group we mean methoxy-, ethoxy-, propoxy-, isopropoxy-, butoxy-, isobutoxy-, secondary-butoxy-, tertiary-butoxy-, preferably ethoxy- or methoxy group.

By a $C_{3-6}$ cycloalkyl group we mean cyclopropyl-, cyclobutyl-, cyclopentyl- or cyclohexyl group.

By 1,3-butadienyl-group we mean (—CH=CH—CH=CH—)-group, ie. the pyridine ring substituted by $R^4$ and $R^5$ substituents means a benzopyridine ring or by its trivial name a quinoline ring.

The heteroaromatic ring containing one or two or three nitrogen atoms means pyrrol, imidazole, pyrazole, 1,2,3-triazole, 1,2,4-triazole, pyridine, pyrimidine, pyridazine, pyrazine and 1,3,4-triazine ring. The ring is optionally substituted by a $C_{1-4}$ alkyl, or alkoxy group or by a halogen atom.

The heteroaromatic ring containing one nitrogen atom and one oxygen or sulphur atom means oxazole, isoxazole, thiazole, isothiazole ring. The ring is optionally substituted by a $C_{1-4}$ alkyl, or alkoxy group or by a halogen atom.

Salts of the compounds of the general formula (I) mean salts given with inorganic and organic acids and bases. Preferred salts are those given with pharmaceutically accepted acids as for instance hydrochloric acid, sulphuric acid, ethanesulphonic acid, tartaric acid, succinic acid, fumaric acid, malic acid, citric acid, and bases, as for instance sodium hydroxide, potassium hydroxide, ethanolamine.

Solvates mean solvates given with various solvents, as for instance with water or ethanol.

The compounds of the general formula (I) show geometric and optical isomerism, therefore the invention also relates to mixtures of the geometric isomers, to racemic or optically active geometric isomers, as well as to their salts and solvates.

A favourable group of the compounds of the general formula (I) is formed by the compounds of the general formula (IA), wherein $R^1$ stands for hydrogen atom or a straight or branched $C_{1-4}$ alkyl group;

$R^2$ stands for hydrogen atom or a straight or branched $C_{1-4}$ alkyl group;

$R^3$ stands for hydrogen atom or a straight or branched $C_{1-4}$ alkyl group, or a phenyl group, thienyl group, or furyl group, optionally substituted by one or more straight or branched $C_{1-4}$ alkyl group, straight or branched $C_{1-4}$ alkoxy group, or halogen atom, or for a 5- or 6 membered heteroaromatic ring—containing one, two or three nitrogen atoms or one nitrogen atom and one oxygen atom or one nitrogen atom and one sulphur atom—optionally substituted by one or more straight or branched $C_{1-4}$ alkyl group, straight or branched $C_{1-4}$ alkoxy group, or halogen atom;

$R^9$, $R^{10}$, $R^{11}$, and $R^{12}$ independently mean hydrogen atom or straight or branched $C_{1-4}$ allyl group, or straight or branched $C_{1-4}$ alkoxy group, or hydroxy group or halogen atom, or $R^9$ and $R^{12}$ stand for hydrogen atom and $R^{10}$ and $R^{11}$ form together a methylenedioxy group;

$R^6$ stands for hydrogen atom or a cyano group, aminocarbonyl group, $C_{1-4}$ alkoxycarbonyl group, or carboxy group;

$R^7$ stands for hydrogen atom or a straight or branched $C_{1-4}$ alkyl group, or a phenyl group, benzyl group, thienyl group or furyl group, optionally substituted by a methylenedioxy group, or one or more straight or branched $C_{1-4}$ alkyl group, straight or branched $C_{1-4}$ alkoxy group, hydroxy group, trifluoromethyl group, cyano group or halogen atom, or for a 5 or 6 membered heteroaromatic ring—containing one, two or three nitrogen atoms or one nitrogen atom and one oxygen atom or one nitrogen atom and one sulphur atom—optionally substituted by one or more straight or branched $C_{1-4}$ alkyl group, straight or branched $C_{1-4}$ alkoxy group, or halogen atom, X stands for a —CH$_2$— group, —NH— group, —NR$^8$— group, or a sulphur atom or an oxygen atom or a sulpho group or a sulphoxy group—wherein $R^8$ stands for a straight or branched $C_{1-4}$ alkyl group or $C_{3-6}$ cycloalkyl group—;

n stands for zero, 1 or 2— and their salts, solvates, optically active isomers and the salts, solvates thereof.

A favourable group of the compounds of the general formula (IA) is formed by the compounds wherein $R^1$ stands for hydrogen atom, or methyl group;

$R^2$ stands for hydrogen atom, or methyl group;

$R^3$ stands for phenyl- or thienyl- or furyl group;

$R^9$, $R^{10}$, $R^{11}$, and $R^{12}$ mean independently hydrogen atom or straight or branched $C_{1-4}$ alkyl group, or straight or branched $C_{1-4}$ alkoxy group, or hydroxy group or halogen atom, or $R^9$ and $R^{12}$ stand for hydrogen atom and $R^{10}$ and $R^{11}$ form together a methylenedioxy group;

$R^6$ stands for hydrogen atom, or cyano group;

$R^7$ stands for 4-methoxyphenyl-, 3-methylphenyl-, 3-methoxyphenyl-, 3-thienyl-, or 3-furyl-group, X stands for —NH— group or for oxygen atom and n stands for 1— and their salts, solvates, optically active isomers and the salts, solvates thereof Especially favourable are the following compounds complying with the above criteria:

3-methyl-N-(4-benzylamino-3-cyanoquinolin-2-yl)benzamide;

4-methoxy-N-(4-benzylamino-3-cyanoquinolin-2-yl)benzamide;

3-methoxy-N-(4-benzylamino-3-cyanoquinolin-2-yl)benzamide;

3,4-methylenedioxy-N-(4-benzylamino-3-cyanoquinolin-2-yl)benzamide;

N-(4-benzylamino-3-cyanoquinolin-2-yl)thiophene-2-carboxamide;

N-(4-[2-thienylmethylamino]-3-cyanoquinolin-2-yl)thiophene-3-carboxamide;

4-methoxy-N-(4-[2-thienylmethylamino]-3-cyanoquinolin-2-yl)benzamide;

3,4-methylenedioxy-N-(4-[2-thienylmethylamino]-3-cyanoquinolin-2-yl)-benzamide;

N-(4-[2-furylmethylamino]-3-cyanoquinolin-2-yl)furan-2-carboxamide;

N-(4-[2-furylmethylamino]-3-cyanoquinolin-2-yl)thiophene-3-carboxamide, and their salts, solvates, optically active isomers and the salts, solvates thereof.

According to another of its aspects, the present invention also relates to pharmaceutical compositions containing as active principles the compounds of the general formula (I) or their isomers, salts and solvates, which are preferably oral compositions, but inhalable, parenteral and transdermal formulations are also subjects of the invention. The above pharmaceutical compositions may be solids or liquides, such as tablets, pellets, capsules, patches, solutions, suspensions or emulsions. The solid compositions, first of all tablets and capsules are the preferred pharmaceutical forms.

The above pharmaceutical compositions are prepared by applying usual pharmaceutical excipients and by using standard methods.

The compounds of the general formula (I) can be used in treating pathologies, in the development of which $A_3$ receptor plays a role.

The compounds of the present invention having selective activity on the $A_3$ receptor can be used in the therapeutic and/or preventive treatment of disfunctions of the heart, kidney, respiratory system, central nervous system. They inhibit the protective effect of adenosine in growing tumor cells, prevent mast cell degranulation, inhibit the cytokine production, reduce the intraocular pressure, inhibit the $TNF\alpha$ release, inhibit the migration of eosinophils, neutrophils and other immune cells, inhibit the bronchoconstriction and plasma extravasation.

Based on these effects, adenosine $A_3$ receptor antagonists of the present invention may be therapeutically useful as antiinflammatory, antiasthmatic, antiischemic, antidepressant, antiarrhytmic, renal protective, antitumor, antiparkinson and cognitive enhancing drugs. They also may be useful in the treatment or prevention of miocardial reperfusion injury, chronic obstructive pulmonary disease (COPD) and adult respiratory distress syndrome (ARDS) including chronic bronchitis, pulmonary emphysema or dyspnea, allergic reactions (e.g. rhinitis, poison ivy induced responses, urticaria, scleroderma, arthritis) other autoimmune diseases, inflammatory bowel disease, Addison's disease, Crohn's disease, psoriasis, rheumatism, hypertension, neurogical function disorders, glaucoma and diabetes (K. N. Klotz, Naunyn-Schmiedberg's Arch. Pharmacol. 362:382,2000; P. G. Baraldi és P. A. Borea, TiPS 21:456, 2000).

The compounds of the present invention may be preferable used for the treatment of diseases such as asthma, COPD and ARDS, glaucoma, tumor, allergic and inflammatory diseases, ischemia, hypoxia, arrythmia and renal diseases.

According to another of its aspects, the present invention relates to the use of the compounds of the general formula (I) in the treatment of the above pathologies. Suggested daily dose is 1–100 mg active ingredient depending on the nature and severeness of the disease and on sex, weight etc. of the patient.

Further subject of the invention is the preparation of the compounds of the general formula (I) and of the intermediates of the general formulae (II) (III) and (IV).

The intermediates of the general formulae (II) (III) and (IV) which are used in the preparation process according to the invention, are partly novel. Substituents of the general formulae (II), (III) and (IV) have the meanings as defined above.

In the process according to our invention the biscarboxamide of the general formula (II) is selectively hydrolysed and the resulting compound of the general formula (I) is, if desired, transformed into its salts, solvates or, liberated from its salt, solvate and separated into its geometric or optical isomers.

Substituents of the compounds of the general formula (I) may be transformed into each other by known methods.

Selective hydrolysis is performed by using alcoholic, preferably methanolic alkali hydroxide solution, preferably potassium and/or sodium hydroxide solutions, but other agents helping the hydrolysis of amides can also be used.

The selective hydrolysis can be carried out in a wide temperature range, favourably between 20° C.–100° C.

The compounds of the general formula (II)—wherein the meanings of $R^1$, $R^2$, $R^3$, $R^4$, $R^5$, $R^6$, $R^7$, $R^8$, X and n are as defined above—can be obtained by several known methods, among them the one demonstrated in Scheme 1 (FIG. 6), by acylation of the compounds of the formula (III), by using an acylation method known in the organic chemistry. For acylating agent preferably acyl chloride, for acid binding agent triethylamine and/or pyiridine can be applied, but other acid binding agents can also be used.

The compounds of the general formula (III)—wherein the meanings of $R^1$, $R^2$, $R^3$, $R^4$, $R^5$, $R^6$, $R^8$, X and n are as defined above—can be prepared from the compounds of the formula (IV)—by using methods known per se (Nan Zhang, Bioorg. and Med. Chem. Lett., 10,2825, 2000).

The compounds of the general formula (IV)—wherein the meanings of $R^4$, $R^5$ and $R^6$ are as defined above—can be prepared from the compounds of the formula (V), by using methods known per se (D. L. Leysen, J. Heterocyclic Chem., 24, 1611, 1987).

The compounds of the general formula (V)—wherein the meanings of $R^4$, $R^5$ and $R^6$ are as defined above—can be prepared from the compounds of the formula (VI), by using methods known per se (Pfizer (Inc) U.S. Pat. No. 4,175,193).

The compounds of the invention, of the general formulae (I), (II), (III) and (IV), their preparation and biological activity are demonstrated in the following Examples, without limiting the scope of claims to the Examples.

Figure 2:
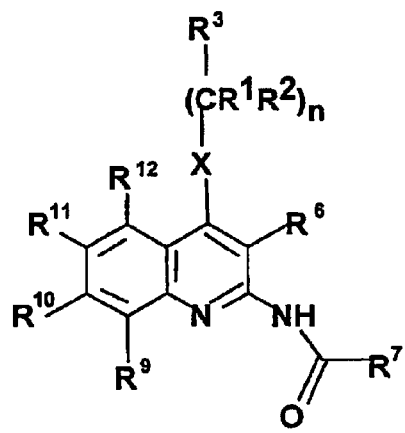
Figure 3:
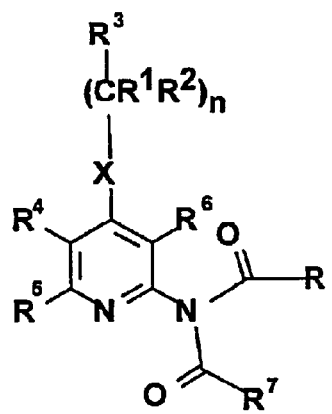
Figure 4:
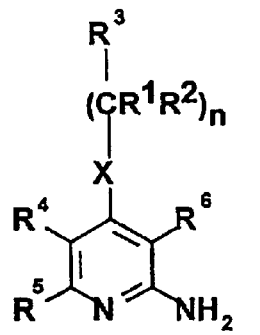
Figure 5:
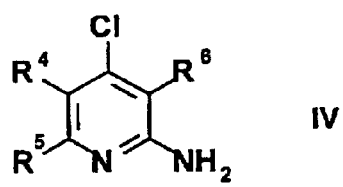
Figure 6:
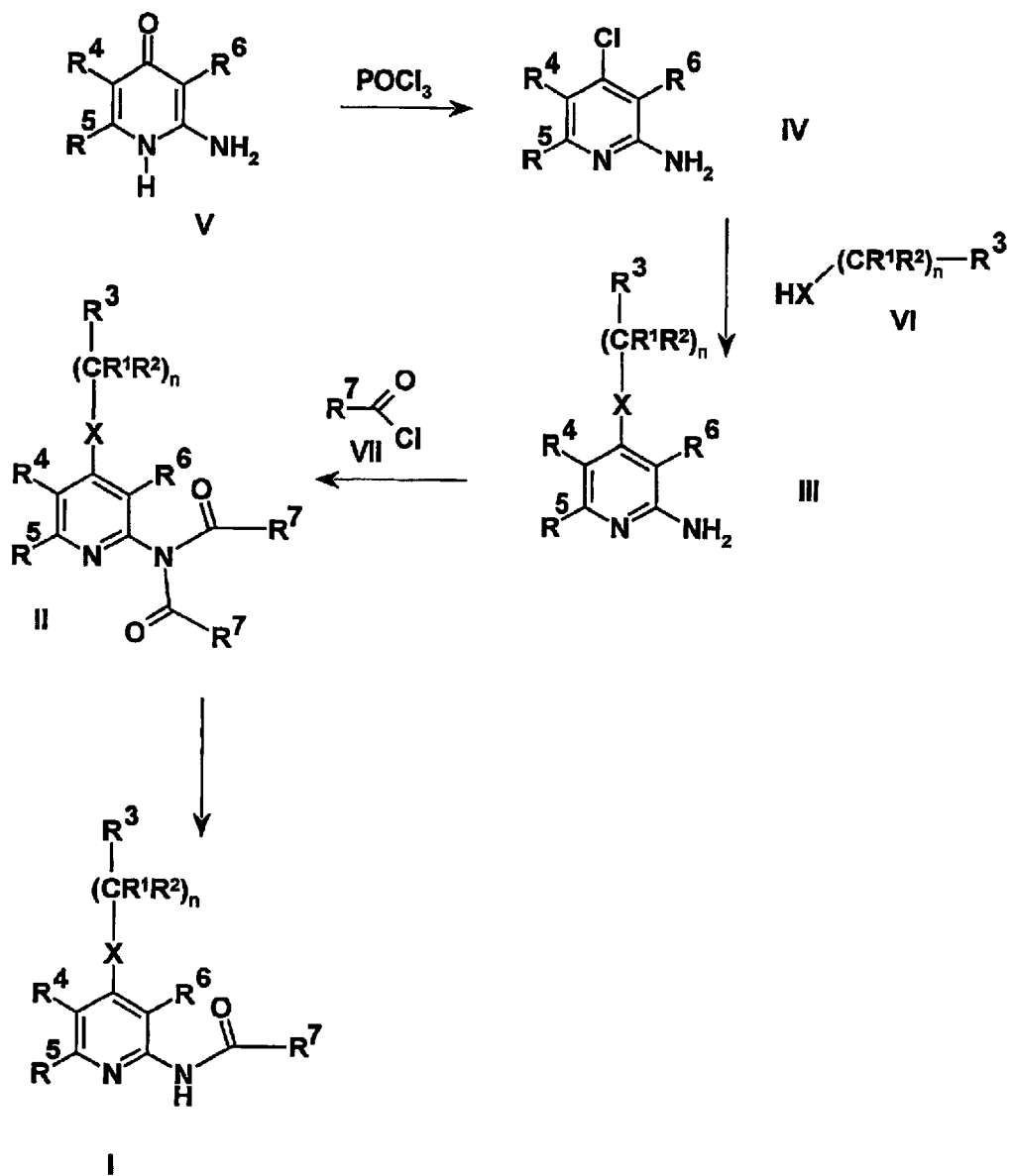

FIG. 1 shows general formula (I),
FIG. 2 shows general formula (IA),
FIG. 3 shows general formula (II),
FIG. 4 shows general formula (III) and
FIG. 5 shows general formula (IV).
FIG. 6 shows Scheme 1 the reaction route for the preparation of compounds of the general formula (I).

EXAMPLES

Example 1

3-Methyl-N-(4-benzylamino-3-cyanoquinolin-2-yl)benzamide

In general formula (I) $R^1$ and $R^2$ stand for hydrogen atoms, $R^3$ for phenyl group, $R^4$ and $R^5$ form together a 1,3-butadienyl group, $R^6$ stands for cyano group, $R^7$ for 3-methylphenyl group, the meaning of X is —NH group, n is 1.

a.) 2-Amino-3-cyano-4-chloroquinoline

The mixture of 10 g of 2-amino-3-cyano-4-hydroxyquinoline and 15 ml of phosphoryl chloride is heated under stirring at 110 ° C. The reaction mixture is cooled down, poured onto 100 ml of ice-water and neutralized with 60 ml of 10% sodium hydroxide solution. The resulting yellow precipitate is filtered off, washed with 50 ml of water. After drying 7.5 g of the title compound is obtained, mp.: 210° C.

NMR, $\delta_H$(400 MHz, DMSO-d$_6$): 7.21 ppm, (s, 2H, NH$_2$), 7.35–7.40 ppm, (dd, 1H, 6-H), 7.53–7.57 ppm, (d, 1H, 5-H), 7.70–7.75 ppm, (dd, 1H, 7-H), 7.93–7.98 ppm, (d, 1H, 8-H)

b.) 2-Amino-3-cyano-4-benzylaminoquinoline 5 g of 2-amino-3-cyano4-chloroquinoline and 11 ml of benzylamine are heated under stirring at 130° C. The reaction mixture is poured onto 50 ml of water, the resulting precipitate is filtered off, washed with 50 ml of water. The pale-yellow precipitate is recrystallized from dimethylformamide to obtain 5.2 g of the title compound.

Mp.: 206° C.

NMR, $\delta_H$(400 MHz, DMSO-d$_6$): 5.02–5.03 ppm, (d, 2H, N—CH$_2$), 6.22 ppm, (s, 2H, NH$_2$), 7.14–7.16 ppm, (dd, 1H, 6-H), 7.24–7.26 ppm, (dd, 1H, 5-H), 7.30 ppm, (s, 5H, Ph), 7.50–7.52 ppm, (dd, 1H, 7-H), 8.16–8.19 ppm, (d, 1H, 8-H), 8.30–8.33 ppm, (t, 1H, NH)

Using 2-aminomethylpyridine or 3-aminomethylpyridine or 4-aminomethylpyridine instead of benzylamine, the appropriate compounds of general formula III can be obtained.

c.) 3-Methyl-N-(3-methylbenzoyl)-N-(4-benzylamino-3-cyanoquinoline-2-yl)benzamide To the solution of 5 g of 2-amino-3-cyano-4-benzylaminoquinoline in 30 ml of pyridine 6 ml of 3-methylbenzoyl chloride are dropped, under stirring at 0° C. The reaction mixture is stirred at 80° C. for 8 hour, then it is poured onto 150 ml of ice-water. The precipitate is filtered off, washed twice with 40 ml of water. The resulting white crystalline material is recrystallized from 200 ml of ethanol to give 9.2 g of the title compound, mp.: 234° C.

By using pyridine-3-carbonyl chloride as acylating agent, the appropriate compound of general formula II can be obtained.

d.) 3-Methyl-N-(4-benzylamino-3-cyanoquinolin-2-yl)benzamide

To the solution of 5 g of 3-methyl-N-(3-methylbenzoyl)-N-(4-benzylamino-3-cyanoquinolin-2-yl)benzamide in 80 ml of acetonitrile 20 ml of 1N methanolic potassium hydroxide solution are added. The reaction mixture is refluxed for 3 minutes, then 3 ml of glacial acetic acid is added to it, then it is neutralized with 50 ml of 1M sodium hydrogen carbonate solution and the resulting crystals are filtered off. The white crystalline material is recrystallized from 130 ml of acetonitrile to give 3.1 g of the title compound of general formula (I). Mp.: 230° C.

Example 2

4-Methoxy-N-(4-benzylamino-3-cyanoquinolin-2-yl)benzamide

In the general formula (I) the meaning of $R^1$ and $R^2$ is hydrogen atom, $R^3$ is phenyl group, $R^4$ and $R^5$ mean together a 1,3-butadienyl group, $R^6$ means cyano group, $R^7$ means 4-methoxyphenyl group, X means —NH— group, n is 1.

2-amino-3-cyano-4-benzylaminoquinoline, prepared as described in Example 1, is transformed with 4-methoxybenzoyl chloride, analogously as described in Example 1, into 4-methoxy-N-(4-methoxybenzoyl)-N-(4-benzylamino-3-cyanoquinolin-2-yl)benzamide, which after selective hydrolysis, by the method described in Example 1, results the title compound of general formula (I). Melting point of the title compound: 188° C.

Sodium salt of the title compound is prepared by the following method:

4-methoxy-N-(4-benzylamino-3-cyanoquinolin-2-yl)benzamide is dissolved in methanol and equivalent amount of sodium hydroxide in methanol is added to it. The precipitated white crystalline material is filtered off. Mp.: 255° C.

Ethanesulfonate salt of the title compound is prepared by the following method: 4-methoxy-N-(4-benzylamino-3-cyanoquinolin-2-yl)benzamide is dissolved in methanol and equivalent amount of ethanesulfonic acid is added to it. The precipitated white crystalline material is filtered off. Mp.: 223° C.

Example 3

3-Methoxy-N-(4-benzylamino-3-cyanoquinolin-2-yl)benzamide

In the general formula (I) the meaning of $R^1$ and $R^2$ is hydrogen atom, $R^3$ is phenyl group, $R^4$ and $R^5$ mean together a 1,3-butadienyl group, $R^6$ means cyano group, $R^7$ means 3-methoxyphenyl group, X means —NH— group, n is 1.

2-amino-3-cyano-4-benzylaminoquinoline, prepared as described in Example 1, is transformed with 3-methoxybenzoyl chloride, analogously as described in Example 1, into 3-methoxy-N-(3 -methoxybenzoyl)-N-(4-benzylamino-3-cyanoquinolin-2-yl)benzamide, which after selective hydrolysis by the method described in Example 1, results the title compound of general formula (I). Melting point of the title compound: 186° C.

Example 4

3,4-Methylenedioxy-N-(4-benzylamino-3-cyanoquinolin-2-yl)benzamide

In the general formula (I) the meaning of $R^1$ and $R^2$ is hydrogen atom, $R^3$ is phenyl group, $R^4$ and $R^5$ mean together a 1,3-butadienyl group, $R^6$ means cyano group, R7 means 3,4-methylenedioxyphenyl group, X means —NH— group, n is 1.

2-amino-3-cyano-4-benzylaminoquinoline prepared as described in Example 1, is transformed with 4-methoxybenzoyl chloride analogously as described in Example 1, into 3,4-methylenedioxy-N-(3,4-methylenedioxybenzoyl)-N-(4-benzylamino-3-cyanoquinolin-2-yl)benzamide which after selective hydrolysis by the method described in Example 1, results the title compound of general formula (I).

Melting point of the title compound: 231° C.

Example 5

N-(4-benzylamino-3-cyanoquinolin-2-yl)thiophene-2-carboxamide

In the general formula (I) the meaning of $R^1$ and $R^2$ is hydrogen atom, $R^3$ is phenyl group, $R^4$ and $R^5$ mean together a 1,3-butadienyl group, $R^6$ means cyano group, $R^7$ means 2-thienyl group, X means —NH— group, n is 1.

2-amino-3-cyano-4-benzylaminoquinoline prepared as described in Example 1. is transformed with thiophene-2-carbonyl chloride, analogously as described in Example 1, into N-(2-thiophenecarbonyl)-N-(4-benzylamino-3-cyanoquinolin-2-yl)thiophene-2-carboxamide, which after selective hydrolysis, by the method described in Example 1, results the title compound of general formula (I).

Melting point of the title compound: 197° C.

Example 6

N-(4-[2-thienylmethylamino]-3-cyanoquinolin-2-yl)thiophene-3-carboxamide

In the general formula (I) the meaning of $R^1$ and $R^2$ is hydrogen atom, $R^3$ is 2-thienyl group, $R^4$ and $R^5$ mean together a 1,3-butadienyl group, $R^6$ means cyano group, $R^7$ means 3-thienyl group, X means —NH— group, n is 1.

a) 2-amino-3-cyano4-(2-thienylmethylamino)quinoline 5 g of 2-amino-3-cyano4-chloroquinoline, prepared as described in Example 1, is stirred with 11 ml of 2-thienylmethylamine at 130° C. for 3 hours. The reaction mixture is poured onto 50 ml of water, the resulting precipitate is filtered off, washed with 50 ml of water. The pale yellow material is recrystallized from 25 ml of ethanol to obtain 5.2 g of title compound, mp.: 208° C.

The 2-amino-3-cyano-4-(2-thienylmethylamino)quinoline prepared as described above is transformed with thiophene-3-carbonyl chloride, analogously as described in Example 1, into N-(3-thiophenecarbonyl)-N-(4-[2-thienylmethylamino]-3-cyanoquinolin-2-yl)-thiophene-3-carboxamide which after selective hydrolysis, by the method described in Example 1, gives the title compound of general formula (I). Melting point of the title compound: 223° C.

Example 7

4-methoxy-N-(4-[2-thienylmethylamino]-3-cyanoquinolin-2-yl)benzamide

In the general formula (I) the meaning of $R^1$ and $R^2$ is hydrogen atom, $R^3$ is 2-thienyl group, $R^4$ and $R^5$ mean together a 1,3-butadienyl group, $R^6$ means cyano group, $R^7$ means 4-methoxyphenyl group, X means —NH— group, n is 1.

The 2-amino-3-cyano-4-(2-thienylmethylamino)quinoline prepared as described in Example 6. is transformed with 4-methoxybenzoyl chloride into 4-methoxy-N-(4-methoxybenzoyl)-N-(4-[2-thienylmethylamino]-3-cyanoquinolin-2-yl)benzamide by the method described in Example 1, which after selective hydrolysis gives the title compound of general formula (I). Melting point of the title compound: 173° C.

Example 8

3,4-methylenedioxy-N-(4-[2-thienylmethylamino]-3-cyanoquinolin-2-yl)-benzamide In the general formula (I) the meaning of $R^1$ and $R^2$ is hydrogen atom, $R^3$ is 2-thienyl group, $R^4$ and $R^5$ mean together a 1,3-butadienyl group, $R^6$ means cyano group, $R^7$ means 3,4-methylenedioxyphenyl group, X means —NH— group, n is 1.

2-amino-3-cyano-4-(2-thienylmethylamino)quinoline prepared as described in Example 6. is transformed with 3,4-methylenedioxybenzoyl chloride into 3,4-methylenedioxy-N-(3,4-methylenedioxybenzoyl)-N-(4-[2-thienylmethylamino]-3-cyanoquinolin-2-yl)benzamide by the method described in Example 1, which after selective hydrolysis gives the title compound of general formula (I). Melting point of the title compound: 241° C.

Example 9

N-(4-[2-furylmethylamino]-3-cyanoquinolin-2-yl)furan-2-carboxamide

In the general formula (I) the meaning of $R^1$ and $R^2$ is hydrogen atom, $R^3$ is 2-furyl group, $R^4$ and $R^5$ mean together a 1,3-butadienyl group, $R^6$ means cyano group, $R^7$ means 2-furyl group, X means —NH— group, n is 1.

a.) 2-Amino-3-cyano4-(2-furylmethylamino)quinoline 5 g of 2-amino-3-cyano-4-chloroquinoline, prepared as described in Example 1 are stirred with 1 ml of 2-furylmethylamine (furfurylamine) at 130° C. for 3 hours. The reaction mixture is poured onto 50 ml of water, the resulting precipitate is filtered off, washed with 50 ml of water. The pale yellow material is recrystallized from 20 ml of ethanol to obtain 4.8 g of the title compound, mp.: 208° C.

The 2-amino-3-cyano-4-(2-furylmethylamino)quinoline prepared as described above is transformed with furan-2-carbonyl chloride by the method described in Example 1. into N-(2-furancarbonyl)-N-(4-[2-furylmethylamino]-3-cyanoquinolin-2-yl) furan-2-carboxamide which after selective hydrolysis gives the title compound of general formula (I). Melting point of the title compound: 196° C.

Example 10

N-(4-[2-furylmethylamino]-3-cyanoquinolin-2yl)thiophene-3-carboxamide

In the general formula (I) the meaning of $R^1$ and $R^2$ is hydrogen atom, $R^3$ is 2-furyl group, $R^4$ and $R^5$ mean together a 1,3-butadienyl group, $R^6$ means cyano group, $R^7$ means 3-thienyl group, X means —NH— group, n is 1. 1.

The 2-amino-3-cyano4-(2-furylmethylamino)quinoline prepared analogously as described in Example 6. is transformed with thiophene-3-carbonyl chloride by the method described in Example 1. into N-(3-thiophene carbonyl)-N-(4-[2-furylmethylamino]-3-cyanoquinolin-2-yl)thiophene-3-carboxamide which after selective hydrolysis, performed analogously as described in Example 1. gives the title compound of general formula (I). Melting point of the title compound: 118° C.

Structure and physical characteristics of further compounds of general formula (I) prepared by the method described in Example 1. are shown in Tables I. and II.

TABLE I
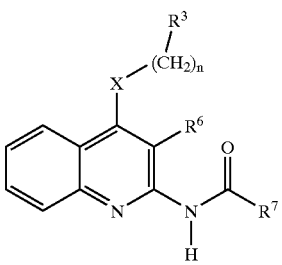
| No.: | X | R³ | R⁶ | R⁷ | n | Mp [° C.] |
|---|---|---|---|---|---|---|
| 11. | NH | 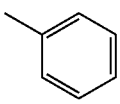 | CN |  | 1 | 237 |
| 12. | NH | 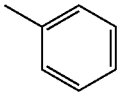 | CN | 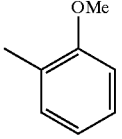 | 1 | 128 |
| 13. | NH | 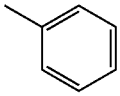 | CN | 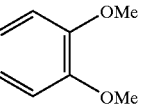 | 1 | 116 |
| 14. | NH | 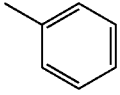 | CN | 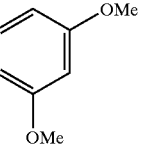 | 1 | 100,5 |
| 15. | NH | 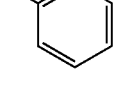 | CN | 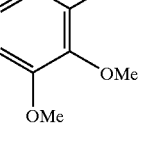 | 1 | 223 |
| 16. | NH | 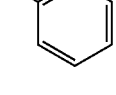 | CN | 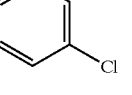 | 1 | 193,5 |
| 17. | NH | 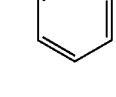 | CN | 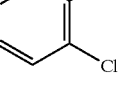 | 1 | 193 |
| 18. | NH | 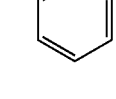 | CN | 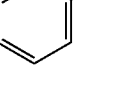 | 1 | 208 |
| 19. | NH | 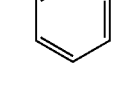 | CN | 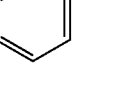 | 1 | 215 |

TABLE I-continued

| No.: | X | R³ | R⁶ | R⁷ | n | Mp [°C.] |
|---|---|---|---|---|---|---|
| 20. | NH | phenyl | CN | 4-cyanophenyl | 1 | 250 |
| 21. | NH | phenyl | CN | 4-methylphenyl | 1 | 205 |
| 22. | NH | phenyl | CN | 3,4-dimethylphenyl | 1 | 238 |
| 23. | NH | phenyl | CN | furan-2-yl | 1 | 212 |
| 24. | NH | phenyl | CN | furan-3-yl | 1 | 215 |
| 25. | NH | phenyl | CN | 3-methylthiophen-? | 1 | 234 |
| 26. | NH | phenyl | CN | benzyl (CH₂-phenyl) | 1 | 160,5 |
| 27. | NH | phenyl | CN | —Me | 1 | 184 |
| 28. | NH | phenyl | CN | CH₂CH₂Me | 1 | 141,5 |
| 29. | NH | phenyl | CN | C(Me)₃ | 1 | 194 |
| 30. | NH | furan-2-yl | CN | phenyl | 1 | 203 |

TABLE I-continued
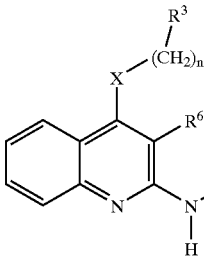
| No.: | X | R³ | R⁶ | R⁷ | n | Mp [° C.] |
|---|---|---|---|---|---|---|
| 31. | NH | 2-furyl | CN | 4-MeO-phenyl | 1 | 152 |
| 32. | NH | 2-furyl | CN | 3-MeO-phenyl | 1 | 190 |
| 33. | NH | 2-furyl | CN | 3,4-methylenedioxyphenyl | 1 | 202 |
| 34. | NH | 2-furyl | CN | 3-Me-phenyl | 1 | 207 |
| 35. | NH | 2-furyl | CN | 3-furyl | 1 | 159 |
| 36. | NH | 2-furyl | CN | 2-thienyl | 1 | 200 |
| 37. | NH | 2-thienyl | CN | 3-MeO-phenyl | 1 | 206 |
| 38. | NH | 2-thienyl | CN | 3-Me-phenyl | 1 | 221 |
| 39. | NH | 2-thienyl | CN | 2-furyl | 1 | 198 |
| 40 | NH | 2-thienyl | CN | 3-furyl | 1 | 158 |
| 41. | NH | 2-thienyl | CN | 2-thienyl | 1 | 178 |

TABLE I-continued

[Structure: quinoline core with X-(CH2)n-R3 at 4-position, R6 at 3-position, and NHC(O)R7 at 2-position]

| No.: | X | R³ | R⁶ | R⁷ | n | Mp [° C.] |
|------|------|-----------------|----|-----------------|---|-------|
| 42. | NH | 2-Cl-phenyl | CN | 4-OMe-phenyl | 1 | 198,5 |
| 43. | NH | 3-Cl-phenyl | CN | 4-OMe-phenyl | 1 | 197,5 |
| 44. | NH | 2-OMe-phenyl | CN | 4-OMe-phenyl | 1 | 191 |
| 45. | NH | 4-OMe-phenyl | CN | 4-OMe-phenyl | 1 | 168,5 |
| 46. | N-Me | phenyl | CN | 4-OMe-phenyl | 1 | 155 |
| 47. | NH | phenyl | H | 4-OMe-phenyl | 1 | 172 |
| 48. | NH | phenyl | H | 3-OMe-phenyl | 1 | 250 |
| 49. | NH | phenyl | H | 3,4-methylenedioxyphenyl | 1 | 264 |
| 50. | NH | phenyl | H | 2-furyl | 1 | 265 |
| 51. | NH | phenyl | H | 2-thienyl | 1 | 163 |

TABLE I-continued

[Structure: quinoline with X-(CH2)n-R3 at 4-position, R6 at 3-position, NH-C(=O)-R7 at 2-position]

| No.: | X   | R³            | R⁶ | R⁷           | n | Mp [° C.] |
|------|-----|---------------|----|--------------|---|-----------|
| 52.  | O   | phenyl        | CN | 4-MeO-phenyl | 1 | 157       |
| 53.  | S   | phenyl        | CN | 4-MeO-phenyl | 1 | 196       |
| 54.  | S=O | phenyl        | CN | 4-MeO-phenyl | 1 | 205       |
| 55.  | NH  | H             | CN | 4-MeO-phenyl | 0 | 266       |
| 56.  | NH  | phenyl        | CN | 4-HO-phenyl  | 1 | 154       |
| 57   | NH  | 2-thienyl     | CN | 4-HO-phenyl  | 1 | 145       |

TABLE II

[Structure: pyridine with NH-CR1R2R3 at 4-position, R4 at 5-position, R5 at 6-position, CN at 3-position, NH-C(=O)-R7 at 2-position]

| R¹ | R² | R³     | R⁴         | R⁵ | R⁷           | Mp [° C.] |
|----|----|--------|------------|----|--------------|-----------|
| 58. Me | H | phenyl | 1-propenyl |    | 4-MeO-phenyl | 165       |

TABLE II-continued
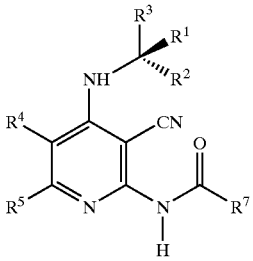
| | R¹ | R² | R³ | R⁴ | R⁵ | R⁷ | Mp [° C.] |
|---|---|---|---|---|---|---|---|
| 59. | H | Me | 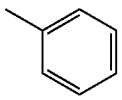 | 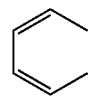 | | 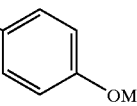 | 145 |
| 60. | H | H | 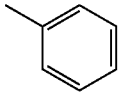 | 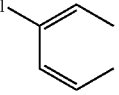 | | 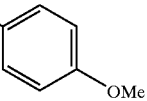 | 119 |
| 61. | H | H | 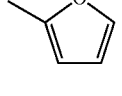 | 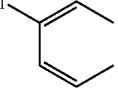 | | 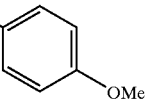 | 119 |
| 62. | H | H | 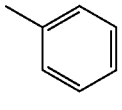 | 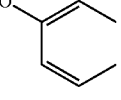 | | 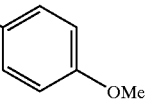 | 243 |
| 63. | H | H | 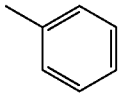 | | 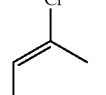 | 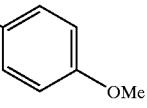 | 176 |
| 64. | H | H | 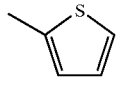 | | 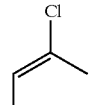 | 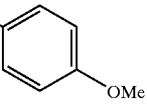 | 171 |
| 65. | H | H | 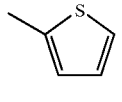 | | 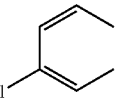 | 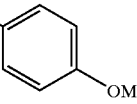 | 199 |
| 66. | H | H | 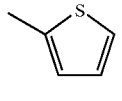 | 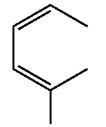 | | 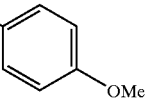 | 203 |
| 67. | H | H | 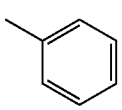 | 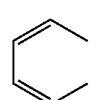 | | 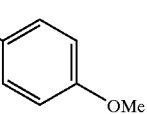 | 180 |

TABLE II-continued

| | R¹ | R² | R³ | R⁴ | R⁵ | R⁷ | Mp [° C.] |
|---|---|---|---|---|---|---|---|
| 68. | H | H | 3-pyridyl | | phenyl | 4-MeO-phenyl | 117 |
| 70. | H | H | 2-thienyl | | 2-Cl-phenyl | 4-MeO-phenyl | 153 |
| 71. | H | H | phenyl | | 3-Cl-phenyl | 4-MeO-phenyl | 215 |
| 72. | H | H | 2-pyridyl | | phenyl | 4-MeO-phenyl | 237 |
| 73. | H | H | 2-thienyl | | 3-MeO-phenyl | 4-MeO-phenyl | 275 |
| 74. | H | H | 2-thienyl | | 2-MeO-phenyl | 4-MeO-phenyl | 245 |
| 75. | H | H | phenyl | | 2-MeO-phenyl | 4-MeO-phenyl | 247 |
| 76. | H | H | phenyl | | 2-MeO-phenyl | 4-MeO-phenyl | 222 |
| 77. | H | H | phenyl | | phenyl | 4-I-phenyl | 218 |
| 78. | H | H | 2-thienyl | | 2-Me-phenyl | 4-MeO-phenyl | 214 |

TABLE II-continued
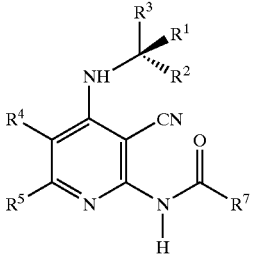
| | R¹ | R² | R³ | R⁴ | R⁵ | R⁷ | Mp [° C.] |
|---|---|---|---|---|---|---|---|
| 79. | H | H | 2-thienyl | | phenyl | 4-iodophenyl | 252 |
| 80. | H | H | 3-iodophenyl | | phenyl | 4-methoxyphenyl | 178 |
| 81. | H | H | 3-iodophenyl | | phenyl | 3-methylphenyl | 173 |
| 82. | H | H | 3-iodophenyl | | phenyl | 2-thienyl | 212 |
| 83. | H | H | 3-iodophenyl | | phenyl | 3-methoxyphenyl | 184 |
| 84. | H | H | 4-pyridyl | | phenyl | 4-methoxyphenyl | 150 |
| 85. | H | H | phenyl | Me | phenyl | 4-methoxyphenyl | 195 |
| 86. | H | H | 2-thienyl | Me | phenyl | 4-methoxyphenyl | 171 |

TABLE II-continued

| | R¹ | R² | R³ | R⁴ | R⁵ | R⁷ | Mp [° C.] |
|---|---|---|---|---|---|---|---|
| 87. | H | H | phenyl | I | | 4-MeO-phenyl | 217 |
| 88. | H | H | 2-thienyl | I | | 4-MeO-phenyl | 149 |
| 89. | H | H | phenyl | I | | 3-Me-phenyl | 135 |
| 90. | H | H | 2-thienyl | I | | 3-Me-phenyl | 127 |
| 91. | H | H | phenyl | I | | 2-thienyl | 257 |
| 92. | H | H | 2-thienyl | I | | 2-thienyl | 260 |
| 93. | H | H | phenyl | I | | 3-thienyl | 153 |
| 94. | H | H | 2-thienyl | I | | 3-thienyl | 145 |
| 95. | H | H | 2-thienyl | MeO | | 4-MeO-phenyl | 214 |
| 96. | H | H | phenyl | MeO | | 4-MeO-phenyl | 183 |

TABLE II-continued
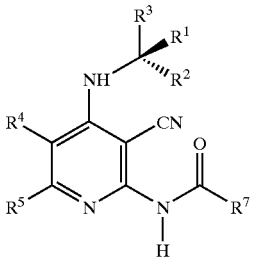
| | R¹ | R² | R³ | R⁴ | R⁵ | R⁷ | Mp [° C.] |
|---|---|---|---|---|---|---|---|
| 97. | H | H | phenyl | H | H | 2-methoxyphenyl | 167 |
| 98. | H | H | phenyl | H | H | 3-methoxyphenyl | 162 |
| 99. | H | H | phenyl | H | H | 4-methoxyphenyl | 183 |
| 100 | H | H | phenyl | H | H | 2-furyl | 216 |
| 101 | H | H | phenyl | H | H | 2-thienyl | 206 |
Structure and physical characteristics of intermediates of general formula (II) prepared by the method described in Example 1. are shown in Table III.
TABLE III
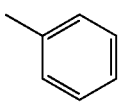
| No.: | X | R³ | R⁶ | R⁷ | Mp [° C.] |
|---|---|---|---|---|---|
| 102 | NH | phenyl | CN | phenyl | 213 |

TABLE III-continued

| No.: | X | R³ | R⁶ | R⁷ | Mp [° C.] |
|---|---|---|---|---|---|
| 103. | NH | phenyl | CN | 2-methoxyphenyl | 208 |
| 104 | NH | phenyl | CN | 3-methoxyphenyl | 178s |
| 105 | NH | phenyl | CN | 4-methoxyphenyl | 158 |
| 106 | NH | phenyl | CN | 3,4-dimethoxyphenyl | 210 |
| 107 | NH | phenyl | CN | 4-methylphenyl | 223 |
| 108 | NH | phenyl | CN | 3,4-dimethylphenyl | 224 |
| 109 | NH | phenyl | CN | 4-cyanophenyl | 212 |
| 110 | NH | phenyl | CN | benzyl | 198 |
| 111 | NH | 2-methoxyphenyl | CN | 4-methoxyphenyl | 208 |
| 112 | NH | 4-methoxyphenyl | CN | 4-methoxyphenyl | 168 |

TABLE III-continued
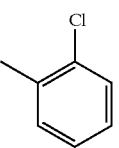
| No.: | X | R³ | R⁶ | R⁷ | Mp [° C.] |
|---|---|---|---|---|---|
| 113 | NH |  2-Cl-C₆H₄ | CN | 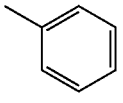 4-OMe-C₆H₄ | 168 |
| 114 | NH |  Ph | CN | 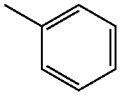 2-furyl | 225 |
| 115 | NH | 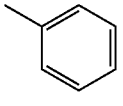 Ph | CN | Me | 152 |
| 116 | NH | 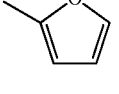 Ph | CN | Et | 192 |
| 117 | NH |  2-furyl | CN | 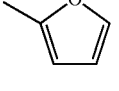 4-OMe-C₆H₄ | 177 |
| 118 | NH |  2-furyl | CN | 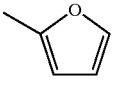 3-OMe-C₆H₄ | 169 |
| 119 | NH | 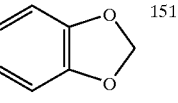 2-furyl | CN | 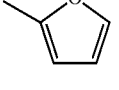 3,4-methylenedioxyphenyl | 151 |
| 120 | NH | 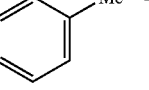 2-furyl | CN | 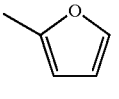 3-Me-C₆H₄ | 218 |
| 121 | NH |  2-furyl | CN | 2-furyl | 194 |
| 122 | NH | 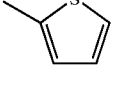 2-thienyl | CN |  4-OMe-C₆H₄ | 188 |

TABLE III-continued
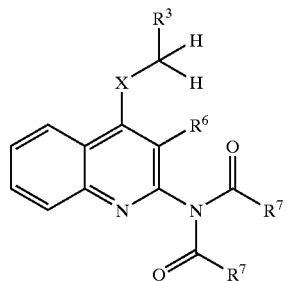
| No.: | X | R³ | R⁶ | R⁷ | Mp [° C.] |
|---|---|---|---|---|---|
| 123 | NH | 2-thienyl | CN | 3,4-methylenedioxyphenyl | 179 |
| 124 | NH | 2-thienyl | CN | 3-methylphenyl | 239 |
| 125 | NH | phenyl | H | 4-methoxyphenyl | 162 |
| 126 | NH | phenyl | H | 3,4-methylenedioxyphenyl | 262 |
| 127 | S | phenyl | CN | 4-methoxyphenyl | 170 |
| 128 | O=S=O | phenyl | CN | 4-methoxyphenyl | 228 |

Structure and physical characteristics of intermediates of general formula (III) and (IIIa) prepared by the method described in Example 1. are shown in Table IV.

TABLE IV

[Structure: pyridine with X-(CR¹R²)ₙ-R³ at position 4, CN at 3, NH₂ at 2, R⁴ at 5, R⁵ at 6]

| No.: | R¹ | R² | R³ | R⁴ | R⁵ | X | n | Mp [° C.] |
|---|---|---|---|---|---|---|---|---|
| 129 | H | H | 2-MeO-phenyl | fused phenyl | | NH | 1 | 192 |
| 130 | H | H | 4-MeO-phenyl | fused phenyl | | NH | 1 | 202 |
| 131 | H | H | 2-Cl-phenyl | fused phenyl | | NH | 1 | 250 |
| 132 | H | H | 3-Cl-phenyl | fused phenyl | | NH | 1 | 167 |
| 133 | H | ⋯Me | phenyl | fused phenyl | | NH | 1 | 183 |
| 134 | H | ▲Me | phenyl | fused phenyl | | NH | 1 | 182 |
| 135 | H | H | phenyl | fused phenyl | | NH | 2 | 172 |
| 136 | H | H | 3,4-diMeO-phenyl | fused phenyl | | NH | 2 | 143 |
| 137 | H | ⋯Me | phenyl | fused phenyl | | NH | 2 | 129 |
| 138 | H | ▲Me | phenyl | fused phenyl | | NH | 2 | 136 |

TABLE IV-continued

[Structure: pyridine with substituents X-(CR¹R²)ₙ-R³ at 4-position, CN at 3-position, NH₂ at 2-position, R⁵ at 6-position, R⁴ at 5-position]

| No.: | R¹ | R² | R³ | R⁴ | R⁵ | X | n | Mp [°C] |
|---|---|---|---|---|---|---|---|---|
| 139 | H | H | phenyl | phenyl | | N—Me | 1 | 212 |
| 140 | H | H | phenyl | phenyl | | S | 1 | 168 |
| 141 | H | H | phenyl | phenyl | | O | 1 | 213 |
| 142 | H | H | phenyl | Cl-phenyl | | NH | 1 | 234 |
| 143 | H | H | furan-2-yl | Cl-phenyl | | NH | 1 | 221 |
| 144 | H | H | phenyl | Me-phenyl | | NH | 1 | 198 |
| 145 | H | H | phenyl | MeO-phenyl | | NH | 1 | 201 |
| 146 | H | H | thiophen-2-yl | Cl-phenyl | | NH | 1 | 213 |
| 147 | H | H | thiophen-2-yl | I-phenyl | | NH | 1 | 198 |
| 147 | H | H | phenyl | I-phenyl | | NH | 1 | 201 |
| 148 | H | H | thiophen-2-yl | Me-phenyl | | NH | 1 | 167 |

TABLE IV-continued
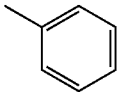
| No.: | R¹ | R² | R³ | R⁴ | R⁵ | X | n | Mp [° C.] |
|---|---|---|---|---|---|---|---|---|
| 149 | H | H | 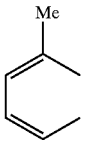 | 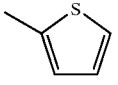 | | NH | 1 | 156 |
| 150 | H | H | 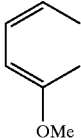 | 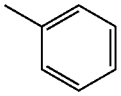 | | NH | 1 | 187 |
| 151 | H | H | 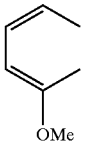 | 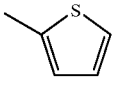 | | NH | 1 | 178 |
| 152 | H | H |  | 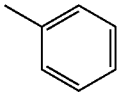 | | NH | 1 | 207 |
| 153 | H | H |  | 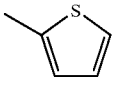 | | NH | 1 | 217 |
| 154 | H | H | 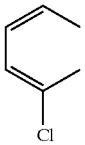 | 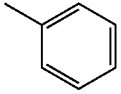 | | NH | 1 | 204 |
| 155 | H | H | 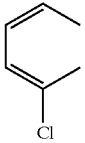 | 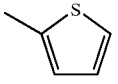 | | NH | 1 | 216 |
| 156 | H | H | 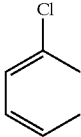 | 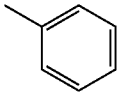 | | NH | 1 | 205 |
| 158 | H | H | 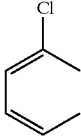 | | | NH | 1 | 213 |

TABLE IV-continued

Structure: pyridine with X-(CR¹R²)ₙ-R³ at 4-position, CN at 3-position, NH₂ at 2-position, R⁴ at 5-position, R⁵ at 6-position.

| No.: | R¹ | R² | R³ | R⁴ | R⁵ | X | n | Mp [° C.] |
|------|----|----|-----|-----|-----|---|---|-----------|
| 159 | H | H | phenyl | 2-hydroxyphenyl | | NH | 1 | 200 |
| 160 | | | phenyl | phenyl | | NH | 0 | 214 |

Structure and physical characteristics of intermediates of general formula (V) prepared by the method described in Example 1. are shown in Table V.

TABLE V

Structure: pyridine with Cl at 4-position, CN at 3-position, NH₂ at 2-position, R⁴ at 5-position, R⁵ at 6-position.

| No: | R⁴ | R⁵ | Mp [° C.] |
|-----|----|----|-----------|
| 161. | 2-hydroxyphenyl | | 360 |
| 162. | 3-chlorophenyl | | 250 |
| 163. | 2-chlorophenyl | | 278 |
| 164. | 2-methylphenyl | | 283 |
| 165. | 2-methoxyphenyl | | 360 |
| 166. | 2-methoxyphenyl | | 234 |
| 167 | 3-methylphenyl | | 246 |
| 168 | 3,5-dimethylphenyl | | 267 |
| 169 | 3-iodophenyl | | 293 |
| 170 | 3-chlorophenyl | | 289 |

TABLE V-continued

[Structure: pyridine with Cl, CN, NH2, R4, R5 substituents]

| No: | R⁴ | R⁵ | Mp [° C.] |
|---|---|---|---|
| 171 | [2-chlorophenyl group] | | 307 |

Example 172

Tablets of the following composition are made by known methods used in the pharmaceutical industry

| | |
|---|---|
| Active ingredient | 25 mg |
| Lactose | 50 mg |
| Avicel | 21 mg |
| Crospovidone | 3 mg |
| Magnesium stearate | 1 mg |

Biology

Methods

Human Adenosine $A_3$ Receptor Binding

Preparing membrane suspension: collect CHO cells expressing $hA_3$ receptors by washing three times with ice cold PBS, centrifugate at 1000×g 10 min, homogenize for 15 sec in buffer (50 mM Tris, 10 mM $MgCl_2$, 1 mM EDTA, pH 8.0), centrifugate at 43,000×g for 10 min (Sigma 3K30), suspense the membrane preparation in the buffer mentioned above, store the aliquots at −80 C.

Binding protocol: incubate CHO-$hA_3$ membrane preparation (2 μg protein content) in incubation buffer (50 mM Tris, 10 mM $MgCl_2$, 1 mM EDTA, 3 U/mL adenosine deaminase, pH 8.0), in the presence of 0.5 nM [$^{125}$I]AB-MECA (p-amino-benzyl-methylcarboxamido-adenosine) (100.000 cpm) and 100 μM R—PIA ($N^6$-[L-2-phenylisopropyl]adenosine) to define non-specific binding or test compound in a total volume of 50 μL for 1 hr at room temperature. Filter over Whatman GF/B glass fibre filters (presoaked in 0.5% polyethylenimine for 3 hours), wash 4× with 1 mL ice-cold 50 mM Tris, 10 mM $MgCl_2$, 1 mM EDTA (pH 8.0) on 96-well Brandel Cell Harvester. Detection of activity: in gamma-counter (1470 Wizard, Wallac). Inhibition [%]=100−((activity in the presence of test compound−non-specific activity)/(total activity−non-specific activity))*100

Human Adenosine $A_1$ Receptor Binding

Preparing membrane suspension: collect CHO cells expressing $hA_1$ receptors by washing three times with ice cold PBS, centrifugate at 1000×g 10 min, homogenize for 15 sec in buffer (50 mM Tris, pH 7.4), centrifugate at 43.000×g for 10 min (Sigma 3K30), suspense the membrane preparation in the buffer mentioned above, store the aliquots at −80° C.

Binding protocol: incubate CHO—$hA_1$ membrane preparation (50 μg protein content) in incubation buffer (50 mM Tris, 3 U/mL adenosine deaminase, pH 7.4), 10 nM [$^3$H] CCPA (2-chloro-$N^6$-cyclopentyl-adenosine) (80,000 dpm) and 10 μM R-PIA ($N^6$-[L-2-phenylisopropyl]adenosine) to define the non-specific binding or test compound in a total volume of 100 μL for 3 hr at room temperature. Filter over Whatman GF/B glass fibre filters (presoaked in 0.5% polyethylenimine for 3 hours), wash 4× with 1 mL ice-cold 50 mM Tris (pH 7.4) on 96-well Brandel Cell Harvester. Detection of activity: in 96-well plate in the presence of HiSafe-3 cocktail in beta-counter (1450 Microbeta, Wallac). Inhibition [%]=100−((activity in the presence of test compound−non-specific activity)/(total activity−non-specific activity))*100

Human Adenosine $A_{2a}$ Receptor Binding

Binding protocol: incubate 7 μg of membranes (human $A_{2a}$ adenosine receptors transfected into HEK-293 cells, source: Receptor Biology, Inc.), buffer (50 mM Tris-HCl, 10 mM $MgCl_2$, 1 mM EDTA, 2 U/mL adenosine deaminase, pH 7.4), 20 nM [$^3$H]CGS-21680 (2-[p-(2-carbonylethyl) phenylethylamino]-5'-N-ethylcarboxamido-adenosine) (200.000 dpm) and 50 μM NECA (5'-N-ethylcarboxamido-adenosine) to define the non-specific binding or test compound in a total volume of 100 μl for 90 min at room temperature. Filter over Whatman GF/B glass fibre filters (presoaked in 0.5% polyethylenimine), wash 4× with 1 mL ice-cold 50 mM Tris, 10 mM $MgCl_2$, 1 mM EDTA, 0.9% NaCl, pH 7.4) on 96-well Brandel Cell Harvester. Detection of activity: in 96-well plate in the presence of HiSafe-3 cocktail in beta-counter (1450 Microbeta, Wallac). Inhibition [%]=100−((activity in the presence of test compound−non-specific activity)/(total activity−non-specific activity))*100

Human Adenosine $A_{2b}$ Receptor Binding

Binding protocol: incubate 20.8 μg of membranes (human $A_{2b}$ adenosine receptors transfected into HEK-293 cells, source: Receptor Biology, Inc.), buffer (50 mM Tris-HCl, 10 mM $MgCl_2$, 1 mM EDTA, 0.1 mM benzamidine, 2 U/mL adenosine deaminase, pH 6.5), 32.4 nM [$^3$H]DPCPX (8-cyclopenthyl-1,3-dipropylxanthine) (800.000 dpm) and 100 μM NECA (5'-N-ethylcarboxamido-adenosine) to define non-specific binding or test compound in a total volume of 100 μL for 30 min at room temperature. Filter over Whatman GF/C glass fibre filters (presoaked in 0.5% polyethylenimine), wash 4× with 1 mL ice-50 mM Tris-HCl (pH 6.5) on 96-well Brandel Cell Harvester. Detection of activity: in 96-well plate in the presence of HiSafe-3 cocktail in beta-counter (1450 Microbeta, Wallac). Inhibition [%]= 100−((activity in the presence of test compound−non-specific activity)/(total activity−non-specific activity))*100

Results

We consider the compounds as biologically active ones if they inhibit the binding of the radioligand on human adenosine $A_3$ receptors with an activity above 80 % at 1 μM in our experimental conditions.

The dissociation constant ($K_d$) of [$^{125}$I]AB-MECA on CHO-$hA_3$ membrane preparation is determined by isotope saturation studies with the help of Scatchard analysis (G. Scatchard, Ann. N.Y. Acad. Sci. 51:660, 1949). The $IC_{50}$ is converted to an affinity constant ($K_i$) by application of the Cheng-Prusoff equation (Y. J. Cheng and W. H. Prusoff, Biochem. Pharmacol. 22:3099, 1973).

Several compounds of the general formula (I), (II), (III) and (IV) display remarkable biological effects. The compounds of the general formula (IA), defined in claim 2, as a subgroup of the general formula (I), defined in claim 1, exert the most important activities. Except of 5 compounds, their $K_i$ values are not higher than 20 nM. The compounds given as examples are especially advantageous. Their $K_i$ values in human adenosine $A_3$ receptor binding studies are between 0.19 and 0.69 nM. The $K_i$ values of the most advantageous compounds are 0.14 and 0.15 nM.

The compounds possess proper bioviabilities and exert at least 10,000-fold selectivity in respect of human adenosine $A_1$, $A_{2a}$ and $A_{2b}$ receptor subtypes.

Further, the duration of their action at intravenous and oral administration is long enough, their $ED_{50}$ values are low, their toxicological and side-effect profiles are advantageous.

Data above make the compounds of the general formula (I) probable for therapeutic applications.

What is claimed is:

1. Compounds of the general formula (I)

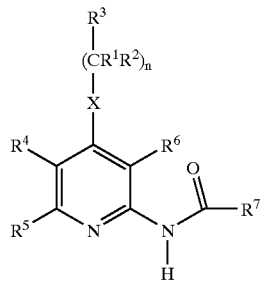

(I)

wherein
- $R^1$ stands for hydrogen atom or a straight or branched $C_{1-4}$ alkyl group;
- $R^2$ stands for hydrogen atom or a straight or branched $C_{1-4}$ alkyl group;
- $R^3$ stands for hydrogen atom or a straight or branched $C_{1-4}$ alkyl group, or a phenyl group, thienyl group, or furyl group, optionally substituted by one or more straight or branched $C_{1-4}$ alkyl group, straight or branched $C_{1-4}$ alkoxy group, or halogen atom, or for one, two or three nitrogen atoms or one nitrogen atom and one oxygen atom or one nitrogen atom and one sulphur atom containing 5- or 6 membered heteroaromatic ring, optionally substituted by one or more straight or branched $C_{1-4}$ alkyl group, straight or branched $C_{1-4}$ alkoxy group, or halogen atom;
- $R^4$ and $R^5$ stand for hydrogen atom or form together an 1,3-butadienyl group, optionally substituted by a methylenedioxy group or one or more straight or branched $C_{1-4}$ alkyl group, straight or branched $C_{1-4}$ alkoxy group, hydroxy group or halogen atom;
- $R^6$ stands for hydrogen atom or a cyano group, aminocarbonyl group, $C_{1-4}$ alkoxycarbonyl group, or carboxy group;
- $R^7$ stands for hydrogen atom or a straight or branched $C_{1-4}$ alkyl group, a phenyl group, benzyl group, thienyl group or furyl group, optionally substituted by a methylenedioxy group, or one or more straight or branched $C_{1-4}$ alkyl group, straight or branched $C_{1-4}$ alkoxy group, hydroxy group, trifluoromethyl group, cyano group or halogen atom, or for one, two or three nitrogen atoms or one nitrogen atom and one oxygen atom or one nitrogen atom and one sulphur atom containing 5 or 6 membered heteroaromatic ring, optionally substituted by one or more straight or branched $C_{1-4}$ alkyl group, straight or branched $C_{1-4}$ alkoxy group, or halogen atom;
- X stands for a —$CH_2$— group, —NH— group, —$NR^8$— group, or a sulphur atom or an oxygen atom or a sulpho group or a sulphoxy group— wherein $R^8$ stands for a straight or branched $C_{1-4}$ alkyl group or $C_{3-6}$ cycloalkyl group—;
- n stands for zero, 1 or 2— and their salts and solvates, optically active isomers and their salts and solvates.

2. Compounds of the general formula (IA)

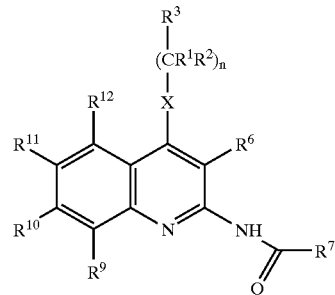

IA according to claim 1—wherein

- $R^1$ stands for hydrogen atom or a straight or branched $C_{1-4}$ alkyl group;
- $R^2$ stands for hydrogen atom or a straight or branched $C_{1-4}$ alkyl group;
- $R^3$ stands for hydrogen atom or a straight or branched $C_{1-4}$ alkyl group, or a phenyl group, thienyl group, or furyl group, optionally substituted by one or more straight or branched $C_{1-4}$ alkyl group, straight or branched $C_{1-4}$ alkoxy group, or halogen atom, or for one, two or three nitrogen atoms or one nitrogen atom and one oxygen atom or one nitrogen atom and one sulphur atom containing 5- or 6 membered heteroaromatic ring, optionally substituted by one or more straight or branched $C_{1-4}$ alkyl group, straight or branched $C_{1-4}$ alkoxy group, or halogen atom;
- $R^9$, $R^{10}$, $R^{11}$ or $R^{12}$ stand independently from each other for hydrogen atom, or straight or branched $C_{1-4}$ alkyl group, straight or branched $C_{1-4}$ alkoxy group, hydroxy group or halogen atom; or
- $R^9$ and $R^{12}$ stand for hydrogen atom and $R^{10}$ and $R^{11}$ form together a methylendioxy group;
- $R^6$ stands for hydrogen atom or a cyano group, aminocarbonyl group, $C_{1-4}$ alkoxycarbonyl group, or carboxy group;
- $R^7$ stands for hydrogen atom or a straight or branched $C_{1-4}$ alkyl group, a phenyl group, benzyl group, thienyl group or furyl group, optionally substituted with a methylenedioxy group, or one or more straight or branched $C_{1-4}$ alkyl group, straight or branched $C_{1-4}$ alkoxy group, hydroxy group, trifluoromethyl group, cyano group or halogen atom, or for one, two or three nitrogen atoms or one nitrogen atom and one oxygen atom or one nitrogen atom and one sulphur atom containing 5 or 6 membered heteroaromatic ring, optionally substituted with one or more straight or branched $C_{1-4}$ alkyl group, straight or branched $C_{1-4}$ alkoxy group, or halogen atom;

X stands for a —CH$_2$— group, —NH— group, —NR$^8$— group, or a sulphur atom or an oxygen atom or a sulpho group or a sulphoxy group—wherein R$^8$ stands for a straight or branched C$_{1-4}$ alkyl group or C$_{3-6}$ cycloalkyl group—;

n stands for zero, 1 or 2— and their salts and solvates, optically active isomers and their salts and solvates.

3. Compounds of the formula (IA) according to claim 2, —wherein

R$^1$ stands for hydrogen atom or a methyl group;

R$^2$ stands for hydrogen atom or a methyl group;

R$^3$ stands for phenyl group, thienyl group or furyl group;

R$^9$, R$^{10}$, R$^{11}$ or R$^{12}$ stand independently from each other for hydrogen atom, or straight or branched C$_{1-4}$ alkyl group, straight or branched C$_{1-4}$ alkoxy group, hydroxy group or halogen atom; or R$^9$ and R$^{12}$ stand for hydrogen atom and R$^{10}$ and R$^{11}$ form together a methylendioxy group;

R$^6$ stands for hydrogen atom or cyano group;

R$^7$ stands for 4-methoxyphenyl group, 3-methylphenyl group, 3-thienyl group or 3-furyl group;

X stands for —NH— group or oxygen atom and n stands for 1— and their salts, solvates and optically active isomers and their salts and solvates.

4. Compounds according to claim 1 chosen from:

3-Methyl-N-(4-benzylamino-3-cyano-quinolin-2-yl) benzamide;

4-Methoxy-N-(4-benzylamino-3-cyano-quinolin-2-yl) benzamide;

3-Methoxy-N-(4-benzylamino-3-cyano-quinolin-2-yl) benzamide;

3,4-Methylenedioxy-N-(4-benzylamino-3-cyano-quinolin-2-yl)benzamide;

N-(4-benzylamino-3-cyano-quinolin-2-yl)thiophene-3-carboxamide;

N-(4-[2-thienylmethylamino]-3-cyano-quinolin-2-yl) thiophene-3-carboxamide;

4-Methoxy-N-(4-[2-thienylmethylamino]-3-cyano-quinolin-2-yl)benzamide;

3,4-Methylenedioxy-N-(4-[2-thienylmethylamino]-3-cyano-quinolin-2-yl)benzamide;

N-(4-[2-furylmethylamino]-3-cyano-quinolin-2-yl)furan-2-carboxamide;

N-(4-[2-furylmethylamino]-3-cyano-quinolin-2-yl) thiophene-2-carboxamide;

and their salts, solvates, optically active isomers and their salts and solvates.

5. Process for the preparation of a compound of the general formula (I), its salts, solvates, optically active isomers and their salts and solvates—wherein in the formula R$^1$, R$^2$, R$^3$, R$^4$, R$^5$, R$^6$, R$^7$, R$^8$, X and n have the same meaning as defined in claim 1, characterized by selective hydrolysis of a bis acid amide of the general formula (II)

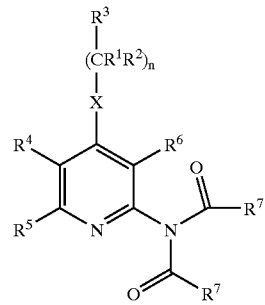

wherein R$^1$, R$^2$, R$^3$, R$^4$, R$^5$, R$^6$, R$^7$, R$^8$, X and n have the same meaning as defined in claim 1— and if desired transforming the substituents of the compound of the general formula (I) thus obtained in each other by methods known per se and/or transforming the compound of the general formula (I) thus obtained into its salts, or solvates, or liberating it from its salts or solvates and/or separating it into its optically active isomeric forms or transforming the optically active forms into the racemic form.

6. Process according to claim 5, characterized by carrying out the selective hydrolysis in an alcoholic medium in the presence of an alkali hydroxide.

7. Pharmaceutical compositions containing as active ingredient one or more compounds of the general formula (I) according to claim 1 or their salts, solvates, or optically active isomers and the salts, solvates thereof, in admixture with one or more excipients used in the pharmaceutical industry.

8. Pharmaceutical compositions containing as active ingredient one or more compounds of the general formula (IA) according to claim 2 or their salts, solvates, or optically active isomers and the salts, solvates thereof, in admixture with one or more excipients used in the pharmaceutical industry.

9. Pharmaceutical composition containing as active ingredient one or more compounds of claim 4 or their salts, solvates, or optically active isomers and the salts or solvates thereof in admixture with one or more excipients used in the pharmaceutical industry.

10. A method for the treatment of asthma, COPD and ARDS, glaucoma, allergic and inflammatory diseases, ischemia, hypoxia, arrhythmia and renal diseases, which comprises administering to a patient in need of such treatment an effective amount of a compound according to claim 1.

11. A method for the treatment of asthma, COPD and ARDS, glaucoma, allergic reactions, inflammatory diseases, ischemia, hypoxia, arrhythmia, and renal diseases, which comprises administering to a patient in need of such treatment an effective amount of a compound according to claim 2.

12. Compounds of the general formula (II)

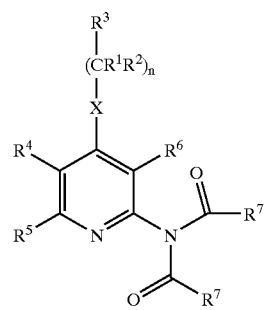

wherein $R^1$, $R^2$, $R^3$, $R^4$, $R^5$, $R^6$, $R^7$, $R^8$, X and n have the same meaning as defined in claim 1.

13. Compounds of the general formula (III)

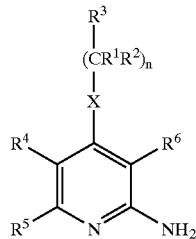

III wherein $R^1$, $R^2$, $R^3$, $R^4$, $R^5$, $R^6$, $R^8$, X and n have the same meaning as defined in claim 1, with the proviso that $R^3$ cannot stand for phenyl group, if $R^1$ and $R^2$ stand for hydrogen atom, n=1, X stands for a —NH— group, $R^4$ and $R^5$ form together an 1,3-butadienyl group and $R^6$ stands for a cyano group, with the further proviso that $R^3$ cannot stand for a hydrogen atom, straight or branched $C_{1-4}$ alkyl group, or a phenyl group, substituted by a straight or branched $C_{1-4}$ alkoxy group, if, n=0, X stands —NH— or —$NR^8$, wherein $R^8$ is as defined in claim 1, $R^4$ and $R^5$ form together a 1,3-butadienyl group and $R^6$ stands for a cyano group, and with the further proviso that $R^3$ cannot stand for hydrogen atom if—, n=0, X stands for a —$CH_2$— group, $R^4$ and $R^5$ form together a 1,3-butadienyl group and $R^6$ stands for a cyano or amino-carbonyl group.

14. Compounds of the general formula (IV)

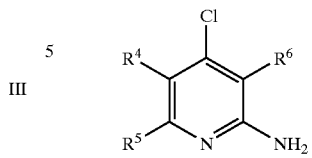

IV wherein $R^4$, $R^5$, and $R^6$ have the same meaning as defined in claim 1, with the proviso that $R^6$ cannot stand for hydrogen atom, if $R^4$ stands for hydrogen atom and $R^5$ stands for a hydrogen atom.

15. Pharmaceutical compositions containing as active ingredient one or more compounds of the general formula (I) according to claim 3 or their salts, solvates, or optically active isomers and the salts, solvates thereof, in admixture with one or more excipients used in the pharmaceutical industry.

16. Process according to claim 6 wherein the alkali hydroxide is potassium or sodium hydroxide.

17. A method for the treatment of asthma, COPD and ARDS, glaucoma, allergic reactions, inflammatory diseases, ischemia, hypoxia, arrhythmia, and renal diseases, which comprises administering to a patient in need of such treatment an effective amount of a compound according to claim 3.

18. A method for the treatment of asthma, COPD and ARDS, glaucoma, allergic reactions, inflammatory diseases, ischemia, hypoxia, arrhythmia, and renal diseases, which comprises administering to a patient in need of such treatment an effective amount of a compound according to claim 4.

\* \* \* \* \*